(12) United States Patent
Batman et al.

(10) Patent No.: US 8,761,941 B2
(45) Date of Patent: Jun. 24, 2014

(54) METHOD FOR DISPLAYING MEDICAL DATA BY A MEDICAL DEVICE DURING DISPLAY FAILURE

(75) Inventors: Carol J. Batman, Indianapolis, IN (US); Michel A. Cadio, Carmel, IN (US); Randy J. Gardner, Bloomington, IN (US); Paul S. Rutkowski, Carmel, IN (US); Mark W. Voth, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/494,294

(22) Filed: Jun. 12, 2012

(65) Prior Publication Data

US 2013/0331675 A1    Dec. 12, 2013

(51) Int. Cl.
*G06F 15/16* (2006.01)

(52) U.S. Cl.
USPC ............... 700/266; 700/17; 700/18; 700/83; 600/365; 340/539.12; 702/19; 702/22; 702/31; 702/32

(58) Field of Classification Search
USPC ........ 700/17, 18, 83, 266; 702/19, 22, 31, 32; 340/539.12; 600/365
See application file for complete search history.

(56) References Cited

U.S. PATENT DOCUMENTS

| | | | |
|---|---|---|---|
| 5,469,070 A | 11/1995 | Koluvek | |
| 5,767,454 A | 6/1998 | Goodwin, III | |
| 7,999,674 B2 | 8/2011 | Kamen | |
| 2006/0087327 A1 | 4/2006 | Ueno et al. | |
| 2007/0116037 A1* | 5/2007 | Moore | 370/462 |
| 2007/0176867 A1 | 8/2007 | Reggiardo et al. | |
| 2008/0040151 A1* | 2/2008 | Moore | 705/2 |
| 2008/0074136 A1 | 3/2008 | Shiraki et al. | |
| 2008/0312584 A1 | 12/2008 | Montgomery et al. | |
| 2010/0323431 A1 | 12/2010 | Rutkowski et al. | |
| 2011/0178820 A1* | 7/2011 | Soni et al. | 705/3 |

* cited by examiner

*Primary Examiner* — Shogo Sasaki
(74) *Attorney, Agent, or Firm* — Harness, Dickey

(57) ABSTRACT

A medical device and a method for displaying medical data by the medical device are disclosed. In one aspect of the disclosure, a method for displaying medical data by a medical device having a display device and one or more processors is disclosed. The method includes monitoring a condition of the display device and determining, at the medical device, whether the display device is in a failure state based on the monitoring, the failure state being indicative of a malfunction of the display device. When the display device is a failure state, the method includes commanding a slave device to display the medical data and providing the medical data from the medical device to the slave device for display by the mobile device.

10 Claims, 11 Drawing Sheets

METHOD FOR DISPLAYING MEDICAL DATA BY A MEDICAL DEVICE DURING DISPLAY FAILURE

FIELD

The present disclosure relates to a medical device and a method for displaying medical data by the medical device, and in particular for displaying medical data when the medical device determines that the display device associated with the medical device is in a failure state.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin and all other factors affecting blood glucose often require a person with diabetes to forecast blood glucose levels. Therefore, therapy in the form of insulin, oral medications, or both can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned blood glucose (bG) meters, continuous glucose monitors, ambulatory insulin infusion pumps, diabetes analysis software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise, and lifestyle. Lab test results include HbA1C, cholesterol, triglycerides, and glucose tolerance. Healthcare professional recommendations include prescriptions, diets, test plans, and other information relating to the treatment of the patient.

In the treatment of the patient, a patient may use a handheld bG meter to obtain his or her bG measurements. The patient may rely on these bG measurements to make treatment decisions, e.g., whether or not to take insulin and if so, how much insulin to take. Thus, the display of medical data such as a bG measurement or an instruction to provide a blood sample is important as the patient may make treatment decisions based on the displayed medical data. An issue may arise, for example, if the display of the handheld bG meter or other medical device is cracked or otherwise damaged, as the medical data may not be properly displayed.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In one aspect of the disclosure, a method for displaying medical data by a medical device having a display device and one or more processors is disclosed. The method includes monitoring a condition of the display device and determining whether the display device is in a failure state based on the monitoring, the failure state being indicative of a malfunction of the display device. When the display device is in a failure state, the method includes commanding a slave device to display the medical data and providing the medical data from the medical device to the slave device for display by the mobile device.

In another aspect of the disclosure, a method for displaying medical data by a medical device having a display device, a blood glucose meter, and one or more processors is disclosed. The method includes monitoring a condition of the display device and determining whether the display device is in a failure state based on the monitoring, the failure state being indicative of a malfunction of the display device. When the display device is in the failure state the method includes commanding a slave device to display an instruction to a patient to insert a blood sample into the blood glucose meter of the medical device, receiving the blood sample, obtaining a blood glucose measurement indicating a blood glucose level of the patient based on the blood sample, and commanding, from the medical device, the slave device to display the blood glucose measurement.

In another aspect of the disclosure, a medical device configured to read blood glucose levels of a patient is disclosed. The medical device includes a display device and a blood glucose meter configured to receive a blood glucose measurement strip containing a blood sample and determine a blood glucose measurement based on the blood sample. The medical device further includes a monitoring module configured to monitor a condition of the display device to determine whether the display device is in a failure state, the failure state being indicative of a malfunction of the display device. The device also includes a communication interface configured to communicate with a slave application executed by a mobile device. The device further includes a control module configured to receive the blood glucose measurement from the blood glucose meter, display the blood glucose measurement on the display device when the display device is not in the failure state, and provide a command to the slave application commanding the slave application to display the blood glucose measurement at the mobile device when the display device is in the failure state.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

Figure 2:
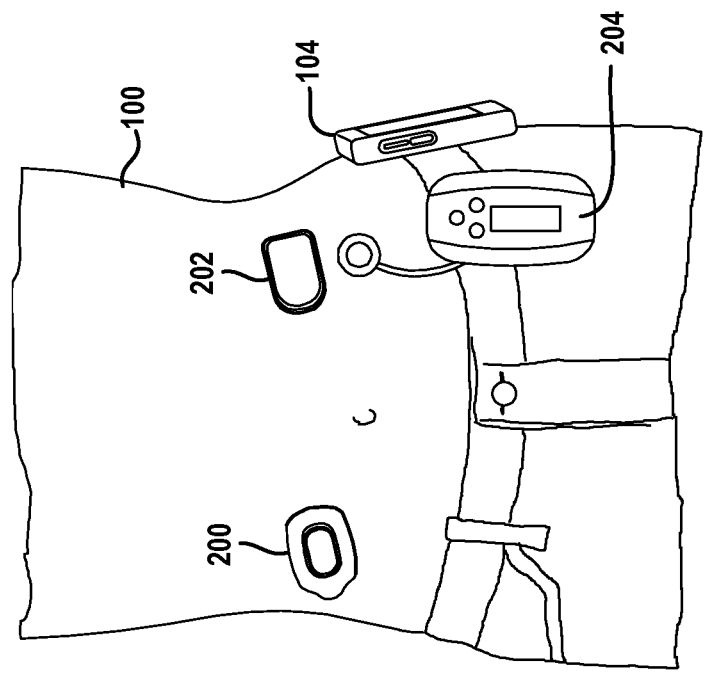
FIG. 2 shows a patient with a continuous glucose monitor (CGM), ambulatory durable insulin infusion pump, ambulatory non-durable insulin infusion pump, and a diabetes manager in accordance with various embodiments of the present disclosure.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Figure 1:
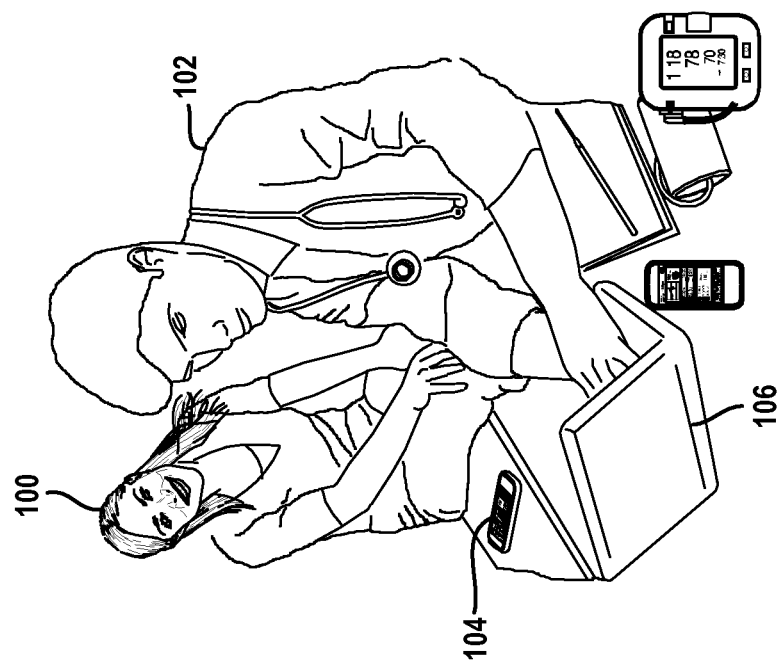
FIG. 1 shows a patient and a treating clinician.

Referring now to FIG. 1, a patient 100 with diabetes and a clinician 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose (bG) measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
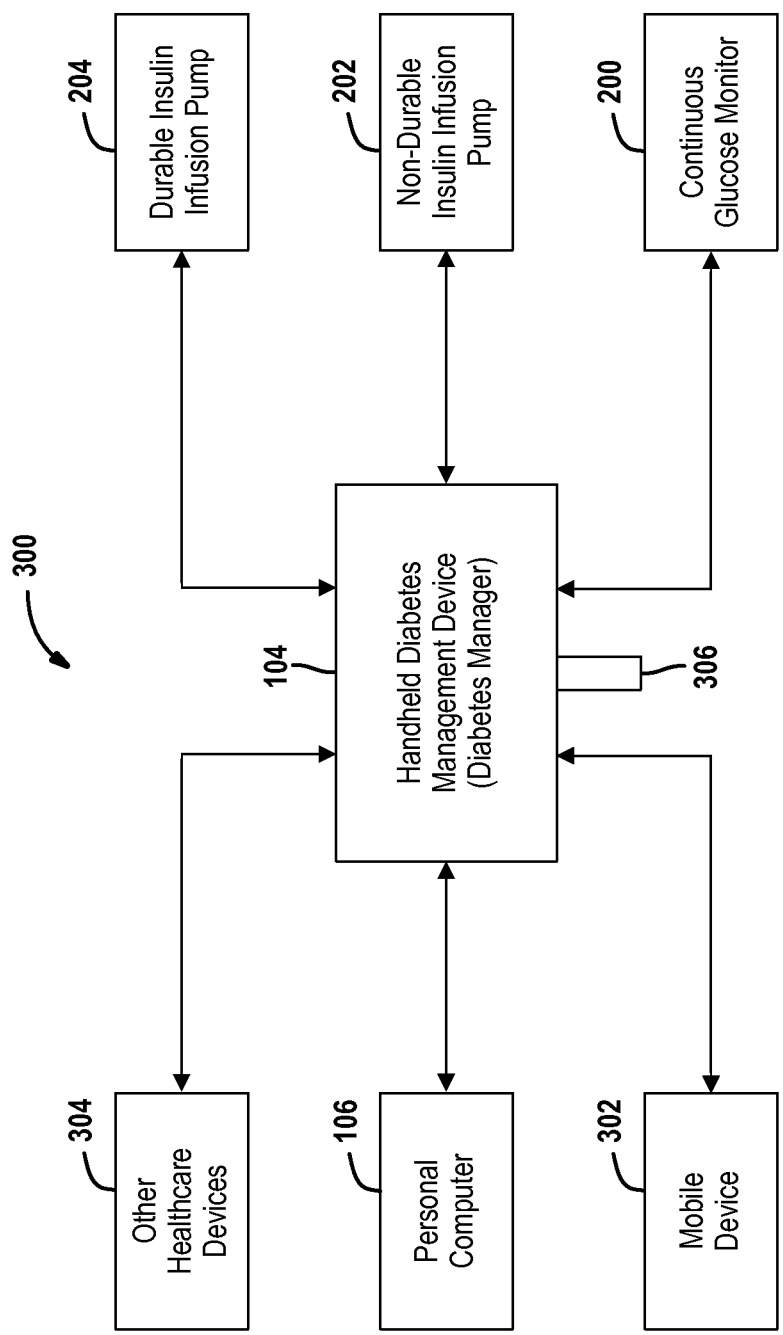
FIG. 3 shows a diabetes care system of systems used by patients and clinicians to manage diabetes in accordance with various embodiments of the present disclosure.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include but are not limited to protocols compliant with the IEEE 11073 standard as extended using guidelines provided by Continua® Health Alliance Design Guidelines. Further, healthcare records systems such as Microsoft® HealthVault™ can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using, for example, a proprietary Gazell wireless protocol developed by Nordic Semiconductor, Inc.

Additionally, the diabetes manager 104 includes a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continua® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a PDA, or a pager. The diabetes manager 104 can send messages to an external network through the mobile device 302. The mobile device 302 can transmit messages to the external network based on requests received from the diabetes manager 104.

Figure 4:
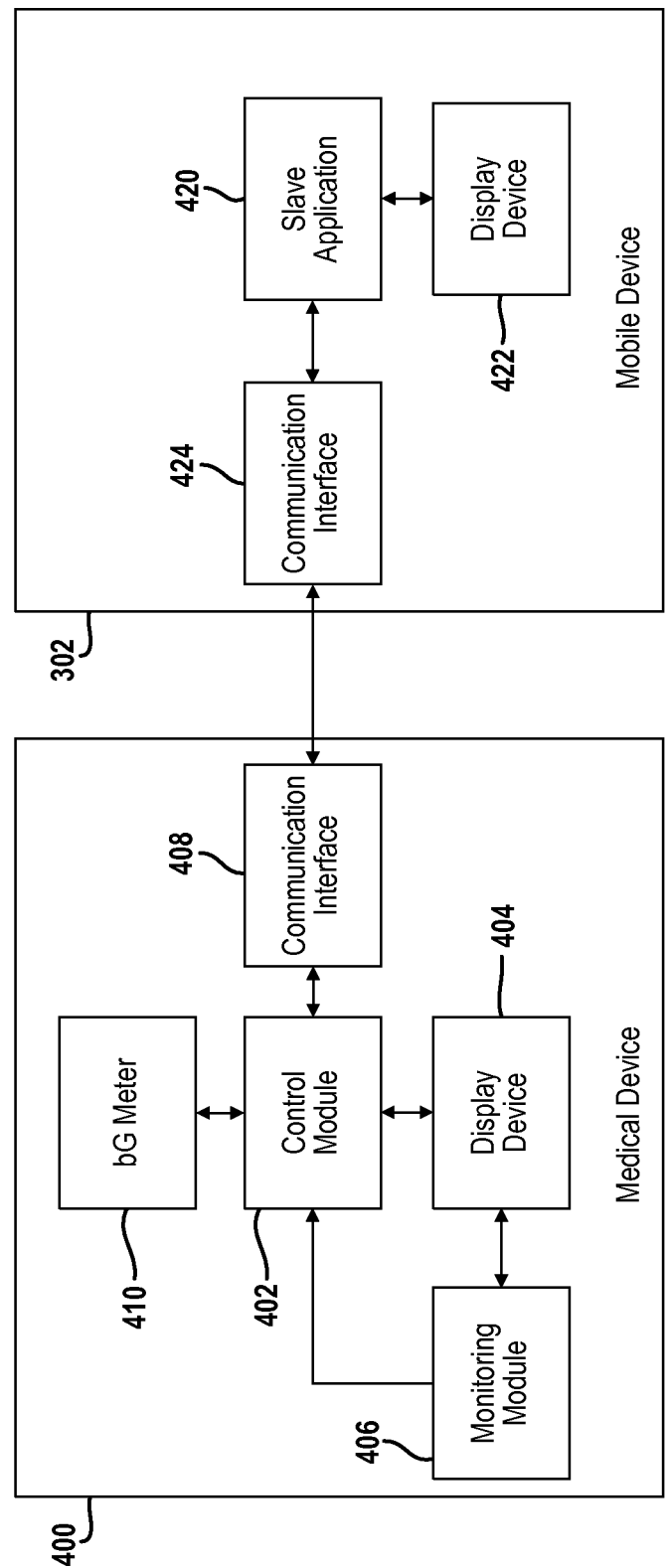
FIG. 4 shows a block diagram illustrating example components of a medical device and a mobile device according to various embodiments of the present disclosure.

Referring now to FIG. 4, a medical device 400 in communication with mobile device 302 is illustrated. For purposes of explanation, it is assumed that the medical device 400 and the mobile device 302 are paired devices, such that communication between the medical device 400 and the mobile device 302 is enabled. In the illustrative example, the medical device 400 is a diabetes manager 104 (as shown FIGS. 1, 2, and 3) and includes a control module 402, a display device 404, a monitoring module 406, a communication interface 408, and a bG meter 410. In the example embodiment, the medical device 400 is configured to monitor a condition of the display device 404 to determine whether the display device 404 is in a failure state. If the display device 404 is determined to be in a failure state, the medical device 400 provides medical data that is to be displayed to the mobile device 302 such that the mobile device 302 displays the medical data. In the illustrative embodiment, the mobile device 302 includes a slave application 420, a display device 422, and a communication interface 424. It is appreciated that the medical device 400 and the mobile device 302 include additional components that are not shown and the components described herein are provided for example and are not intended to be exhaustive.

As mentioned above, in the illustrative example the medical device 400 is a diabetes manager 104. Thus, the medical device 400 includes the bG meter 410. The bG meter 410 receives a bG measurement strip 306 (FIG. 3), which the patient doses with a blood sample, and determines a bG measurement based on blood sample. The bG measurement is provided to the control module 402 for display on the display device 404.

The display device 404 can be any device capable of electronically displaying data. The display device 404 is integrated within the medical device 400 such that a screen of the display device 404 is located at a front surface of the medical device 400. In some embodiments, the display device 404 is a touchscreen that displays data and can detect the presence of a touch within the display area. In these embodiments, the display device 404 can be a capacitive touchscreen, an infrared touchscreen, resistive touchscreen, or any other type of touchscreen. In other embodiments the display device 404 is an LCD display and the medical device 400 may also include a user interface (not shown) such as a keyboard or physical buttons. The display device 404 may also include a display cache (not shown) which caches information that is to be displayed by the display device 404.

In the illustrative embodiment, the monitoring module 406 monitors the condition of the display device 404 to determine whether the display device 404 is in a failure state. A failure state can be a condition where the display device 404 has malfunctioned such that the display device 404 is unable to reliably display medical data due to the malfunction. For example, the display device 404 can be said to be in a failure state if the screen of the display device 404 is cracked or broken, the backlight of the display device 404 is burnt out, or the display cache of the display device 404 has failed. It should be appreciated that the foregoing list of conditions which may result in a failure state is non-exhaustive and not intended to be limiting. When the monitoring module 406 determines that the display device 404 is in a failure state, the monitoring module 406 provides a notification to the control module 402 indicating the same.

In the illustrated example, the control module 402 is configured to control the operation of the medical device 400. In this example, the medical device 400 is a diabetes manager 104. Thus, the control module 402 can determine when a patient is to be prompted to provide a blood sample, perform structured testing, determine any corrective actions that may be taken based on a bG reading, and/or perform any other suitable tasks. Further, the control module 402 is configured to display medical data on the display device 404. In the case of a diabetes manager 104, the control module 402 can provide medical data, e.g., bG measurements determined by the bG meter 410 or instructions to the patient for providing a blood sample, for display by the display device 404. If, however, the monitoring module 406 determines that the display device 404 is in a failure state, the control module 402 transmits a command to the mobile device 302 to operate in a slave mode, such that the medical device 400 vis-à-vis the control module 402 displays the medical data on the mobile device 302.

As will be discussed in greater detail below, the mobile device 302 is configured to act as a slave device and the medical device 400 is configured to act as a master device when the display device 404 is in a failure state. Thus, in the exemplary embodiment the control module 402 is configured to provide commands to the mobile device 302 to display the medical data. The commands can include the medical data which is to be displayed by the mobile device 302. Furthermore, the control module 402 can provide a command to the mobile device 302 to display a graphical user interface (GUI) to the patient such that the patient can interact with medical device 400 via a user interface of the mobile device 302. In some embodiments, the control module 402 may also provide a command to the mobile device 302 to transmit a notification of the malfunctioned display device 404 to a server (not shown) of the medical device 400 manufacturer. In these embodiments, the medical device 400 manufacturer can receive notification of the malfunctioned display device 404 and can send a replacement medical device 400 to the patient in an efficient manner.

It should be appreciated that the control module 402 can be configured to perform additional corrective actions when the display device 404 is in the failure state. For example, the control module 402 can generate a visual or audible notification to the patient, thereby informing the patient of the failure state. Alternatively or additionally, the control module 402 can turn the display device 404 off. In some embodiments, when the display device 404 is in a failure state, the control module 402 may transfer one or more data records to the mobile device 402 or another device, e.g., a PC, such that any important patient records are stored and available at the other device. Other corrective actions may also be performed.

In the illustrated example, the communication interface 408 is configured to effectuate communication with one or more other devices, including the mobile device 302. The communication interface 408 can implement any suitable communication protocol. For example, the communication interface 408 can be a Bluetooth® transceiver, an 802.11 transceiver, an infrared transceiver, or any other suitable transceiver. Alternatively, the communication interface 408 can be a wired communication interface such as a USB interface. In the illustrative embodiment, the control module 402 provides commands to the mobile device 302 via the communication interface 408.

The mobile device 302 can be any suitable mobile device, including but not limited to a mobile telephone, a tablet computing device, a personal digital assistant (PDA). As should be appreciated the display device 422 of the mobile device 302 can be any suitable display, including but not limited to a touchscreen or an LCD display.

The mobile device 302 receives commands from the medical device 400 via the communication interface 424 of the mobile device 302. As should be appreciated, mobile devices 302 are typically configured to support numerous different communication protocols. Thus, the communication interface 424 can include a Bluetooth® transceiver, an 802.11 transceiver, an infrared transceiver, and/or any other suitable transceiver. Alternatively, the communication interface 424 can be a wired communication interface such as a USB interface. The communication interface 424 receives commands from the medical device 400 and provides the commands to the slave application 420.

In an exemplary embodiment, the slave application 420 is an application that is executed by one or more processors (not shown) on the mobile device 302. The slave application 420 can be downloaded to and/or installed on the mobile device 302 by the patient. The slave application 420 can be provided by the manufacturer of the mobile device 302 or a third-party. In some embodiments, the slave application 420 may execute as a background process and may receive a notification from the medical device 400 that the display device 404 of the medical device 400 is in a failure state. In response to the notification, the slave application 420 may be automatically launched or a visual notification may be displayed to the patient on the display device 422 of the mobile device 302 instructing the patient to launch the slave application 420. Alternatively, the operating system of the mobile device 302 may be configured to receive the notification from the medical device 400 and may automatically launch the slave application 420 upon receiving the notification or may provide the visual notification to the patient instructing the patient to launch the slave application 420.

Once the slave application 420 is launched, the mobile device 302 can be said to be operating in a slave mode, such that the slave application 420 is controlled at least in part by the medical device 400. Thus, the slave application 420 receives commands from the medical device 400 and performs actions defined in the commands. Thus, the slave application 420 can include one or more GUI screens that can be displayed by the display device 422 of the mobile device 302. For example, in some embodiments the slave application 420 can display a GUI screen that replicates a GUI displayed by the display device 404 of the medical device 400. In these embodiments, the slave application may receive a command to display a GUI screen. In response, the slave application 420 displays the GUI screen on the display device 422 of the mobile device 302.

As was discussed, the medical device 400 provides commands to the slave application 420 to display medical data. In some embodiments, the commands can include the type of medical data that is to be displayed and/or the medical data to be displayed. For example, if the medical device 400 provides a command to display a bG measurement, the command may include the value of the bG measurement as well as an indicator that the medical data is a bG measurement to be displayed. In response to the command, the slave application 420 can display a screen for displaying bG measurement values on the display device 422 and can display the received bG measurement value therein.

In another example, the medical device 400 may provide a command to the slave application 420 to display an instruction to the patient to provide a blood sample. In this example, the command may include the instruction to be displayed as well as an indicator that the medical data is an instruction to provide a blood sample. In response to the command, the slave application 420 can display a GUI screen that includes the instruction to provide a blood sample on the display device 422 of the mobile device 302. It should be appreciated that an instruction to provide a blood sample includes any technique for collecting a blood sample, including but not limited to, prompting the patient to insert a blood strip and to dose the blood strip with the blood sample after insertion, and prompting the patient to insert an already dosed blood sample. Furthermore, in some embodiments the displayed GUI screen may include a visual button where the patient can verify that the patient has provided the blood sample, e.g., the patient has inserted a blood glucose measurement strip 306 in the bG meter 410. If the patient presses the visual button, the slave application 420 can transmit a verification indicating that the patient has provided the blood sample to the medical device 400 via the communication interface 424.

The foregoing examples are provided to illustrate the types of medical data that the slave application 420 can display on the display device 422 of the mobile device 302 and are not intended to be limiting. It should be appreciated that the slave application 420 can be configured to display other types of medical data depending on the type of medical device 400. For instance, if the medical device 400 is a blood pressure machine the medical data that is displayed may relate to a blood pressure measurement. Furthermore, the mobile device 302 may receive commands from the medical device 400 to display additional information, such as an instruction to contact the medical device 400 manufacturer and a phone number of the medical device 400 manufacturer. In these embodiments, the patient may call the medical device 400 manufacturer to quickly obtain a replacement medical device 400 or a replacement part.

Further, it is appreciated that while FIG. 4 depicts a mobile device 302, the slave application 420 can be implemented on any suitable device that can execute the slave application 420 and has a display device 422 and a communication interface 424, such that the medical device 400 can be paired with the device executing the slave application 420. For example, the slave application 420 may be executed by a personal computer or a television.

Figure 5:
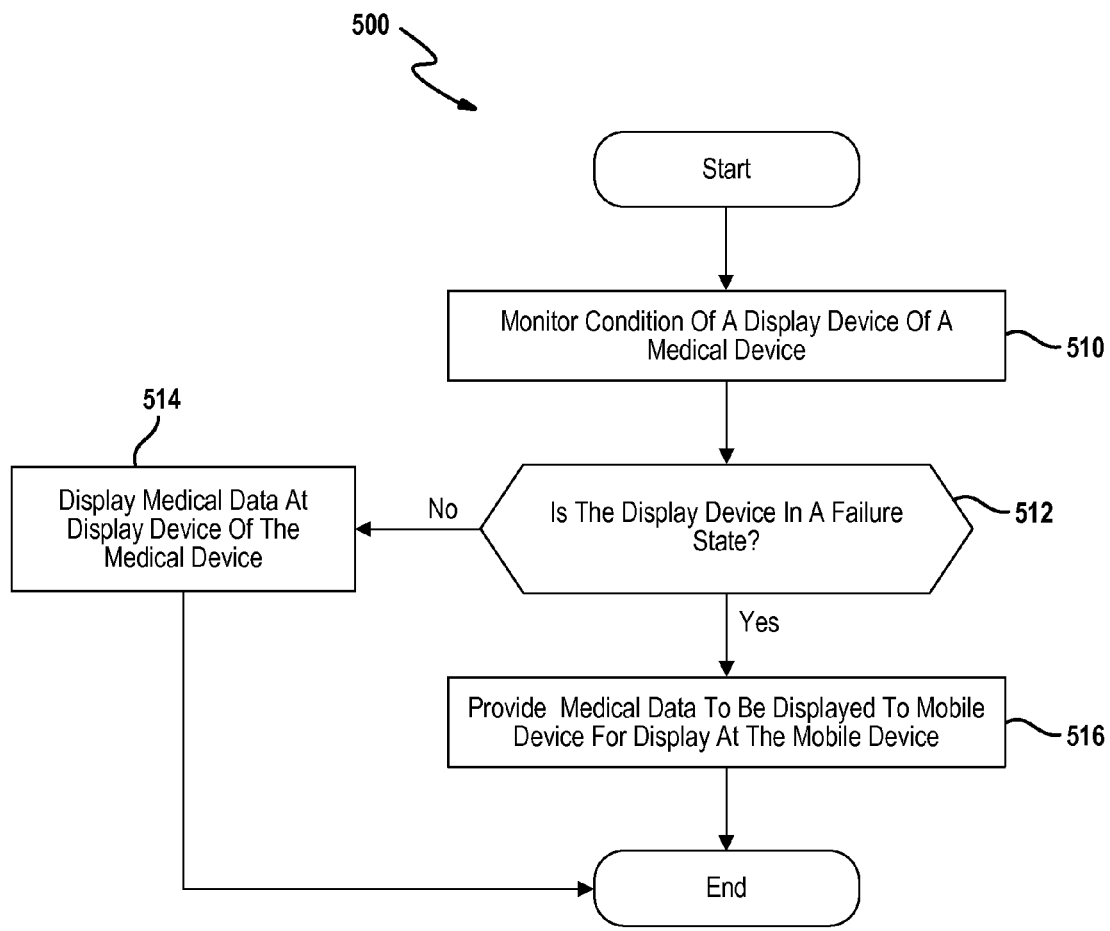
FIG. 5 shows a flow chart illustrating an exemplary method for displaying medical data according to various embodiments of the present disclosure.

FIG. 5 illustrates an exemplary method 500 for displaying medical data that may be executed by a medical device 400. At step 510, the medical device 400 monitors the condition of its display device 404. For instance, the medical device 400 can monitor various components of the display device 404 to determine whether a screen of the display device 404 is cracked or whether the display device 404 has otherwise malfunctioned, e.g., a damaged backlight or a malfunctioned display cache. The medical device 400 determines whether the display device 404 is in a failure state based on the monitoring, as shown at 512. If the medical device 400 determines that the display device 404 is not in a failure state, the medical device 400 displays medical data on the display device 404, as shown at 514.

If, however, the medical device 400 determines that the display device 404 is in a failure state, e.g., the medical device determines that the screen of the display device 404 is cracked, the medical device 400 begins to provide medical data that is to be displayed to a mobile device 302 for display at the mobile device 302, as shown at 516. As discussed, the mobile device 302 can have a slave application 420 installed thereon that receives commands from the medical device 400. Upon determining that the display device 404 is in a failure state, the medical device 400 provides a command to the slave application 420 to operate in a slave mode. Once the slave application 420 begins operating in mobile device 302 slave mode, the medical device 400 provides commands to display medical data to the slave application 420, which in turn displays the medical data on the mobile device 302. Medical data may also be communicated via other methods such as audio.

The method 500 provided above may be executed each time the medical device 400 is to display medical data, when the medical device 400 is powered on, or at predetermined time intervals, e.g. each hour. Further, it should be appreciated that the foregoing method 500 is provided for example and not intended to be limiting. Variations of the method 500 are contemplated and are within the scope of this disclosure.

Figure 6:
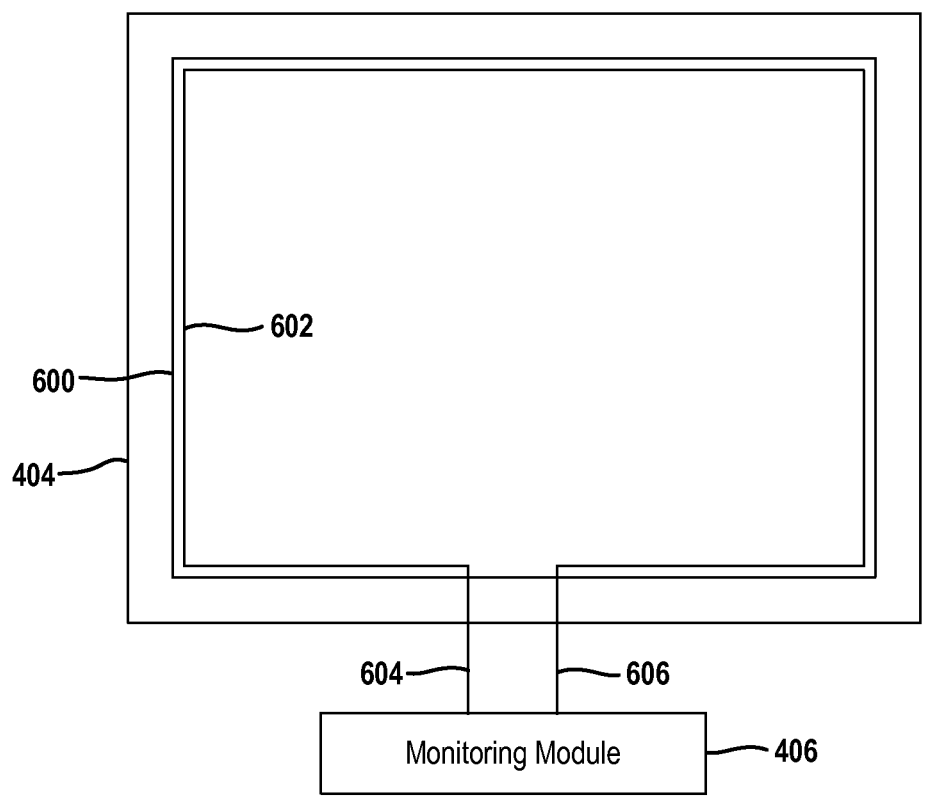
FIG. 6 shows a drawing illustrating an example configuration of a monitoring module that monitors the condition of a screen of a display device of a medical device according to various embodiments of the present disclosure.

Referring now to FIG. 6, an example configuration of the monitoring module 406 in relation to a screen 600 of the display device 404. In the illustrated example, the monitoring module 406 is configured to determine if the screen of the display device 404 is cracked. In the exemplary embodiment, a conductive loop 602 is integrated along a peripheral edge of the screen 600. In an example embodiment, the conductive loop 602 can be a thin wire made from indium tin oxide. It should be appreciated that the conductive loop 602 can be made from any other suitable conductive material which can be formed into a thin wire. In the case of an LCD display or a touchscreen display, the conductive loop 602 can be integrated along the peripheral edge of a glass or plastic panel of the screen 600, such that if the glass or plastic panel is cracked or broken the conductive loop 602 also breaks.

The monitoring module 406 is coupled to the conductive loop 602 at a first end 604 of the conductive loop 602 and at a second end 606 of the conductive loop 602. In operation, the monitoring module 406 emits a monitoring signal, e.g., an electronic signal, at the first end 604 of the conductive loop 602 and monitors the second end 606 of the conductive loop 602. If the monitoring signal is received by the monitoring module 406 at the second end 606, the monitoring module 406 determines that the screen 600 is not cracked. If, however, the monitoring signal is not received at the second end 606, the monitoring module 406 determines that the screen 600 is cracked and provides a notification of the cracked screen 600 to the control module 402.

It is further appreciated that the monitoring module 406 may further monitor other conditions of the display device 404, as was described in relation to FIGS. 4 and 5.

Figure 7:
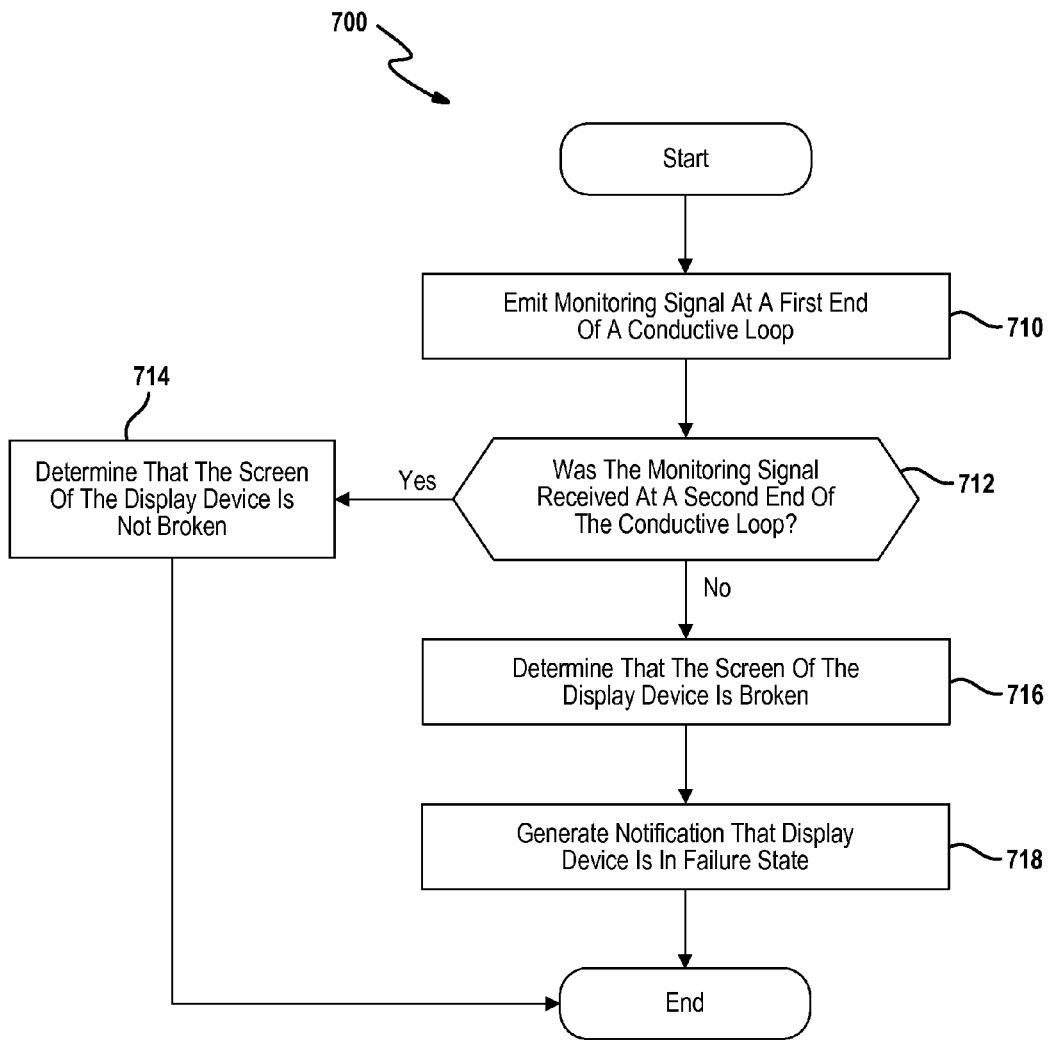
FIG. 7 shows a flow chart illustrating an exemplary method for monitoring the condition of a screen of a display device of a medical device according to various embodiments of the present disclosure.

FIG. 7 illustrates an example method 700 for monitoring a condition of a screen 600 of a display device 404 of a medical device 400. The illustrated method 700 can be performed by the monitoring module 406 configured as illustrated in FIG. 6. In the illustrative example the monitoring module 406 emits the monitoring signal at the first end 604 of the conductive loop 602, as shown at 710. The monitoring module 406 then determines whether the monitoring signal was received at the second end 606 of the conductive loop 602, as shown at 712. If the monitoring signal was received at the second end 606 of the conductive loop 602, the monitoring module 406 determines that the screen 600 is not broken, as shown at 714. If, however, the monitoring signal was not received at the second end 606 of the conductive loop 602, the monitoring module 406 determines that the screen 600 is broken, as shown at 716. When the monitoring module 406 determines that the screen 600 is broken, the monitoring module 406 can notify the control module 402 that the display device 404 is in a failure state as a result of the broken screen 600, as shown at 718. For example, the monitoring module 406 can provide a signal to the control module 402 indicating that the screen 600 is broken.

It is appreciated that the method 700 described above is provided for example only and not intended to be limiting. Variations of the method 700 are contemplated and are within the scope of the disclosure. Further, the monitoring module 406 can execute additional methods for monitoring other conditions of the display device 404.

Figure 8:
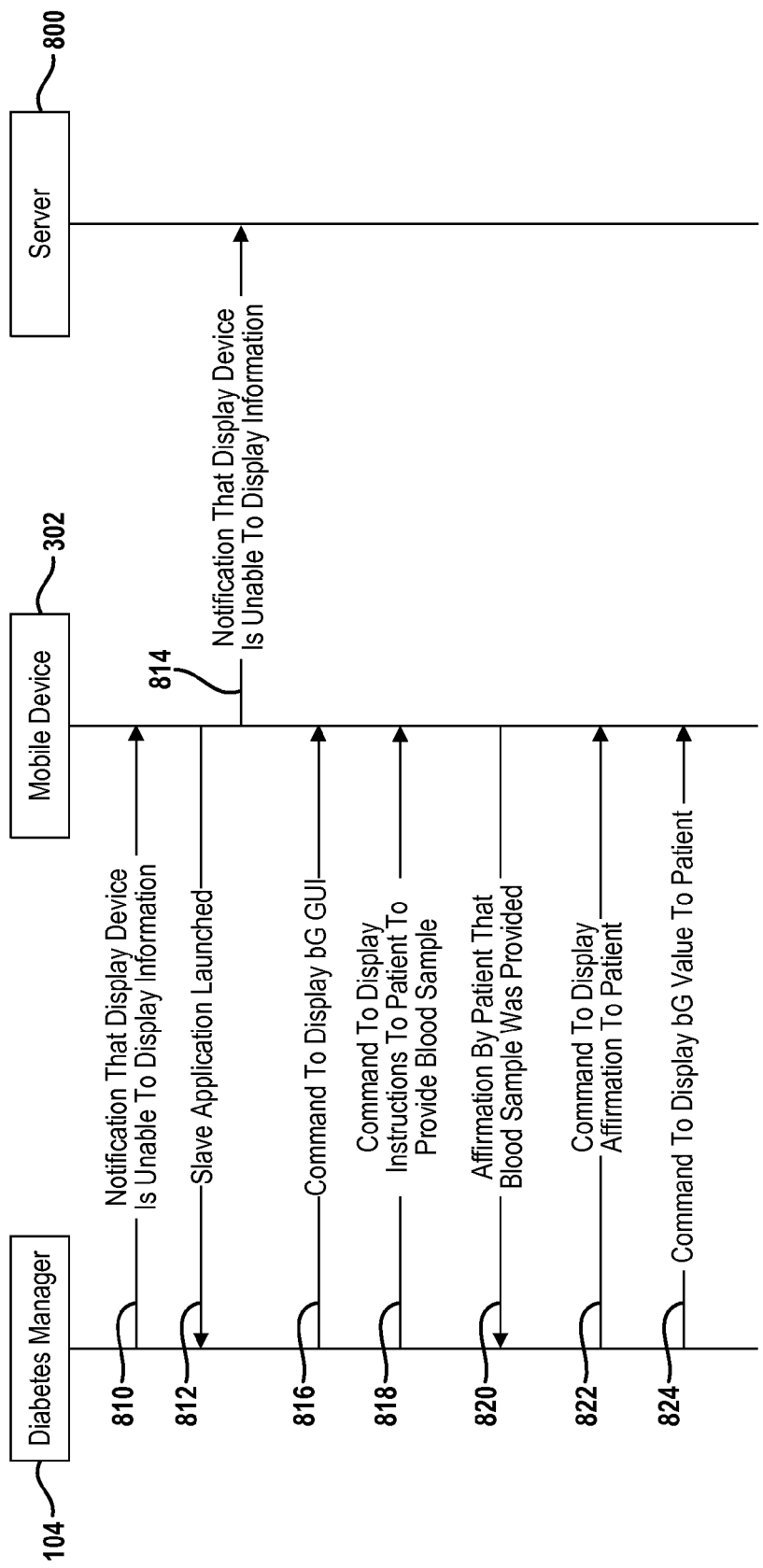
FIG. 8 shows a diagram illustrating example communications between a medical device, a slave device, and a server according to various embodiments of the present disclosure.

Referring now to FIG. 8, an example of a sequence of communications that may be performed between a diabetes manager 104 (medical device 400), a mobile device 302, and a server 800 affiliated with the manufacturer of the diabetes manager 104 upon determining that the display device 404 is in a failure state. FIG. 8 is described in view of FIGS. 9A-9D. FIGS. 9A-9D illustrate a diabetes manager 104 having a cracked screen 600. The diabetes manager 104 is paired to and in communication with the mobile device 302, which is executing the slave application 420 (FIG. 4).

At communication 810, the diabetes manager 104 provides a notification to the mobile device 302 indicating that the display device 404 of the diabetes manager 104 is in a failure state. The notification may be or may include a command to launch the slave application 420. As was discussed above, the mobile device 302 may launch the slave application 420 in response to the notification.

At communication 812, the mobile device 302 may provide a verification indicating that the slave application 420 was launched. Furthermore, in response to receiving the notification that the display device 404 is in the failure state, the mobile device 302 may provide a notification that the display device 404 is in a failure state to the server 800, as shown at communication 814.

At communication 816, the diabetes manager 104 may provide a command to the mobile device 302 to display a GUI screen at the mobile device 302. In response to communication 816, the mobile device 302 displays the GUI screen indicated by the command.

Figure 9A:
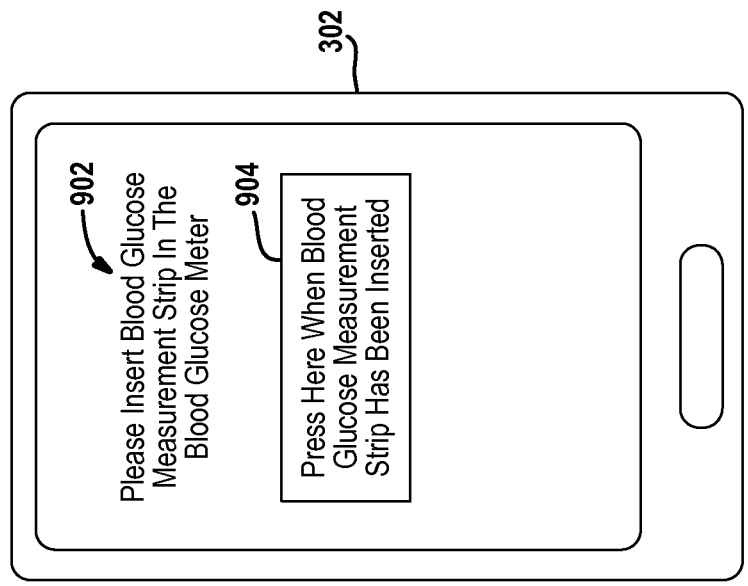
FIGS. 9A-9D show drawings illustrating of an example user interface that may be displayed by a mobile device when the display device of a medical device is malfunctioned.
Figure 9A:
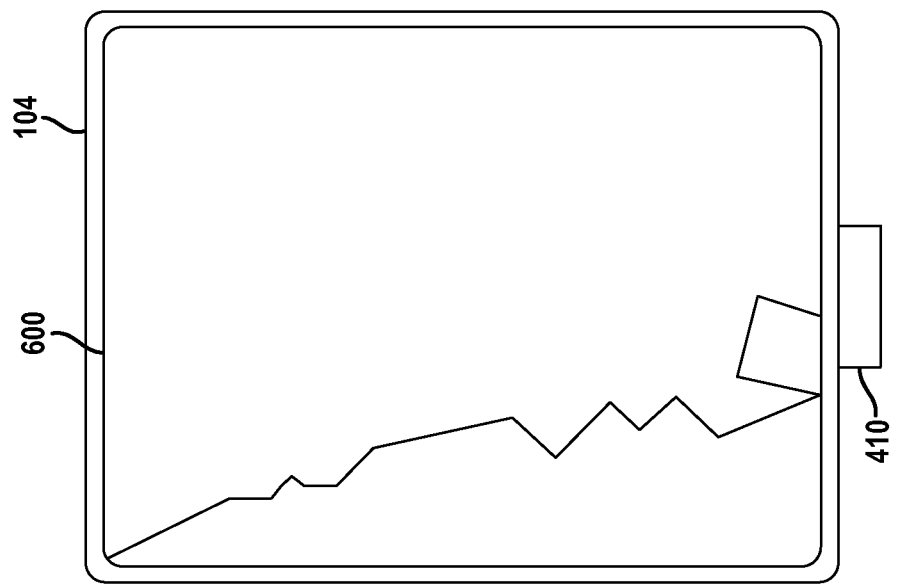

At communication 818, the diabetes manager 104 may provide a command to the mobile device 302 to display instructions within the GUI screen, such that the instructions instruct the patient to provide a blood glucose measurement strip 306 to the diabetes manager 104. In response to communication 818 the mobile device 302 displays the instructions in the GUI screen. As shown in FIG. 9A, the mobile device 302 is displaying a GUI screen containing an instruction 902 to the patient to insert a blood glucose measurement strip 306 in the bG meter 410. As illustrated, the GUI screen includes a button 904 that the patient can press to verify that the blood glucose measurement strip 306 has been inserted in the bG meter 410.

As was discussed above, the GUI screen presented by the mobile device 302 may include a button for the patient to press when the patient has provided the blood glucose measurement strip 306 to the diabetes manager 104. Thus, when the patient presses the button, the mobile device 302 may provide an affirmation to the diabetes manager 104 indicating that the blood glucose measurement strip 306 has been provided, as shown at communication 820.

Figure 9B:
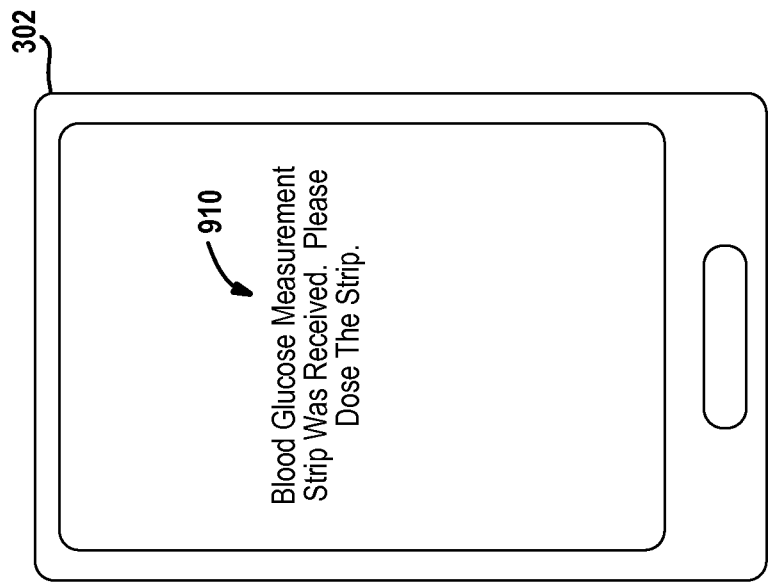
Figure 9B:
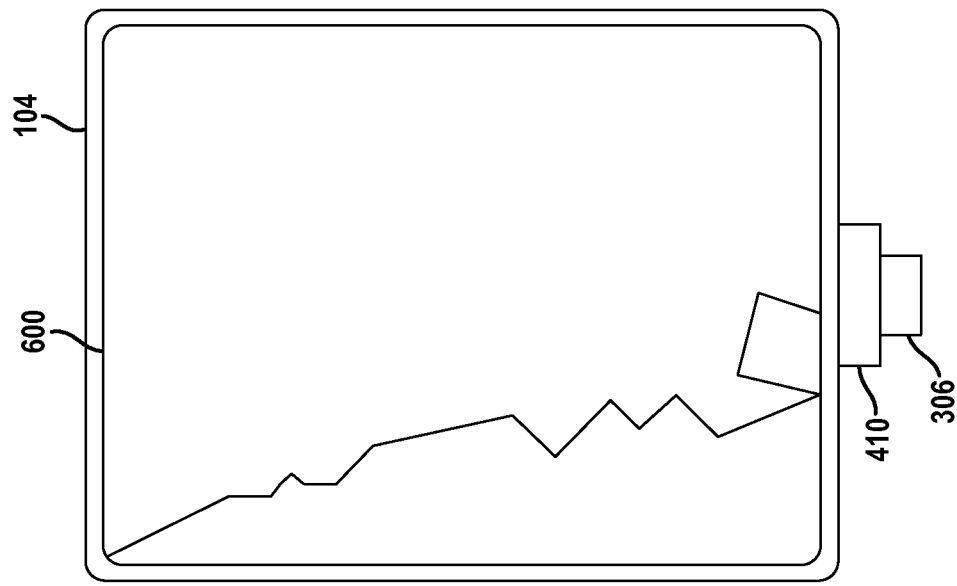
Figure 9C:
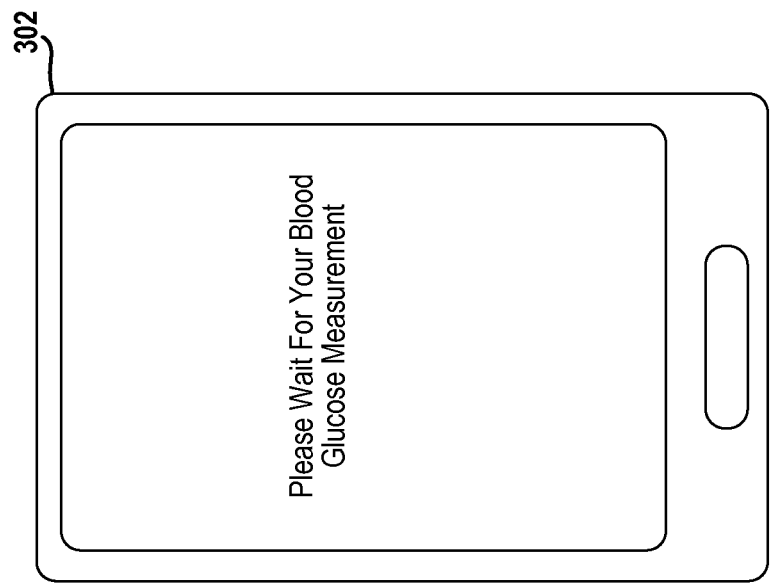
Figure 9C:
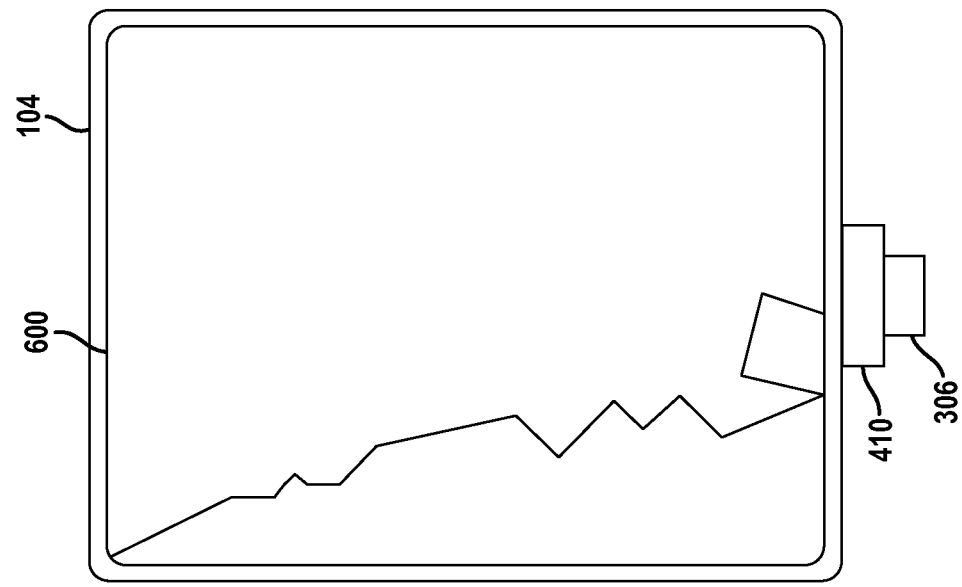

Upon receiving the affirmation from the mobile device 302, the diabetes manager 104 may determine whether a bG measurement strip 306 was properly inserted into the bG meter 410. If the bG measurement strip 306 was properly inserted into the bG meter 410, the diabetes manager 104 provides a command to the mobile device 302 to display an affirmation to the patient that the bG measurement strip 306 was received, as shown at communication 822. In response to communication 822, the mobile device 302 displays the affirmation. As illustrated in FIG. 9B, the bG measurement strip 306 has been inserted in the bG meter 410. Thus, the GUI screen displayed by the mobile device 302 displays an affirmation 910 indicating that the bG measurement strip 306 was received by the diabetes manager 104. Furthermore, the affirmation may include an instruction to the patient to "dose" the measurement strip, that is instructing the patient to provide a blood sample to the bG meter 410 via the strip 306. While the bG meter 410 is determining the blood glucose level, the diabetes manager 104 may command the mobile device 302 to display a screen indicating that the blood glucose measurement is being determined, as shown in FIG. 9C.

Figure 9D:
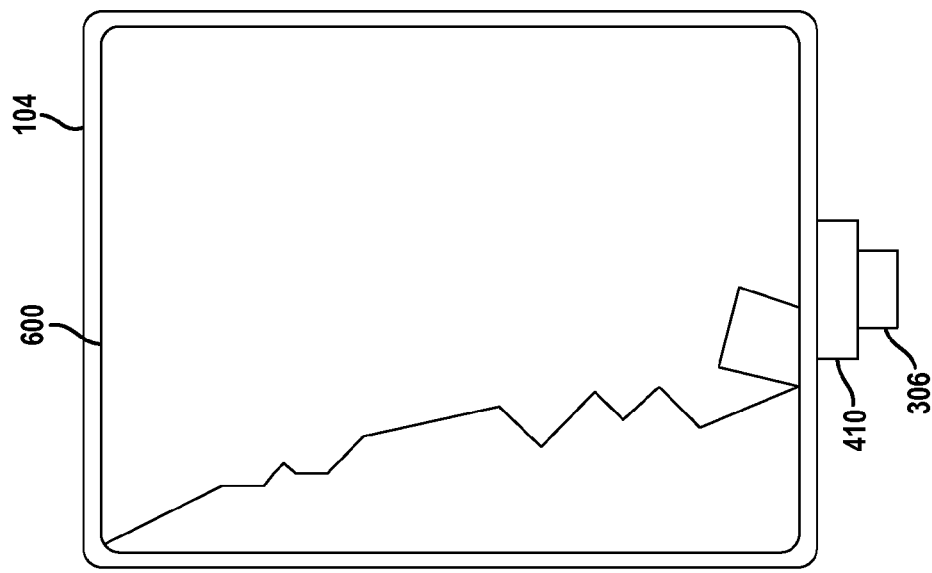
Figure 9D:
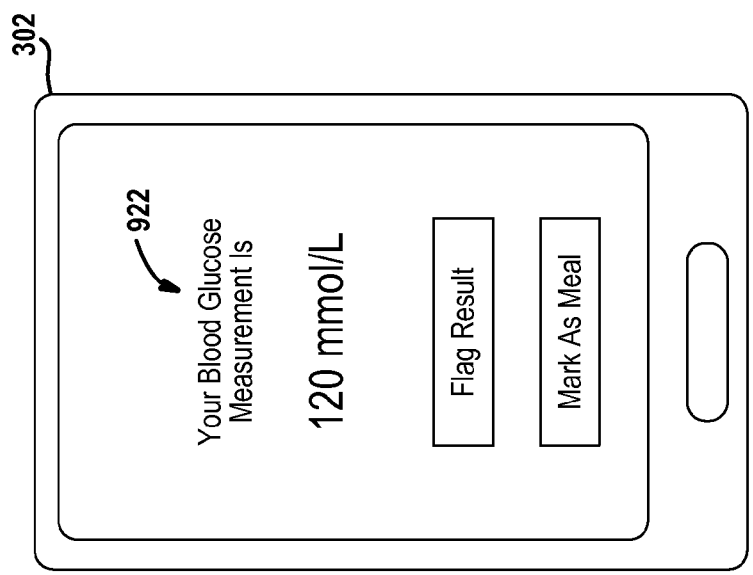

If and when the diabetes manager 104 obtains a bG measurement from the blood sample provided on the bG measurement strip 306, the diabetes manager 104 provides a command to the mobile device 302 to display the bG measurement value to the patient, as shown at communication 824. In response to communication 824, the mobile device 302 displays the bG measurement value. As depicted in FIG. 9D, the mobile device 302 displays the bG measurement 922 to the patient. In the example, the GUI displayed by the mobile device 302 (at the command of the diabetes manager 104) may include additional buttons 924 and 926 for the patient to flag the result or mark as a meal. It should be appreciated that additional or alternative buttons may also be displayed by the mobile device 302.

It should be appreciated that the sequence provided above is provided for example only. The sequence should not be viewed as limiting as various sequences are contemplated and are within the scope of the disclosure. Further, it is appreciated that the medical device 400 (diabetes manager 104) can be further configured to command the mobile device 302 to display additional data. For example, the medical device 400 may command the mobile device 302 to display a screen where an instruction to call the medical device 400 manufacturer is displayed, as well as the telephone number of the medical device 400 manufacturer.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A method for displaying medical data from a medical device comprising:
    monitoring, at the medical device, a condition of a display unit of the medical device;
    determining, at the medical device, whether the display unit is in a failure state based on the monitoring, the failure state being indicative of a malfunction of the display unit; and
    transmitting, by the medical device, a command to display the medical data via a data communication link to a mobile device paired with the medical device, where the mobile device includes another display unit and the transmitting is in response to a determination that the display unit of the medical device is in the failure state.

2. The method of claim 1, wherein the medical device is a blood glucose meter.

3. The method of claim 1, wherein the display unit includes an electrically conductive loop integrated around a peripheral edge of the display unit.

4. The method of claim 3, further comprises:
    emitting, at the medical device, a monitoring signal at a first end of the conductive loop;
    monitoring, at the medical device, a second end of the conductive loop; and
    determining, at the medical device, whether the display unit is in the failure state based on absence of the monitoring signal at the second end of the conductive loop.

5. The method of claim 1, further comprises, commanding, by the medical device, the mobile device to provide a notification to a manufacturer of the medical device, the notification indicating the failure state.

6. A method for displaying medical data from a medical device having a blood glucose meter, and one or more processors, the method comprising:
    monitoring, at the medical device, a condition of a display unit of the medical device;
    determining, at the medical device, whether the display unit is in a failure state based on the monitoring, the failure state being indicative of a malfunction of the display unit;
    transmitting, by the medical device, a command to display an instruction to provide a blood sample via a data communication link to a mobile device paired with the medical device, where the mobile device includes another display unit and the transmitting is in response to a determination that the display unit of the medical device is in the failure state;
    receiving, at the blood glucose meter of the medical device, the blood sample;
    obtaining, at the medical device, a blood glucose measurement indicating a blood glucose level of the patient based on the blood sample; and
    transmitting, by the medical device, a command to display the blood glucose measurement to the mobile device.

7. The method of claim 5, wherein the display unit includes an electrically conductive loop integrated around a peripheral edge of the display unit.

8. The method of claim 7 further comprises:
    emitting, at the medical device, a monitoring signal at a first end of the conductive loop;
    monitoring, at the medical device, a second end of the conductive loop; and
    determining, at the medical device, whether the display unit is in the failure state based on absence of the monitoring signal at the second end of the conductive loop.

9. The method of claim 6 further comprises, commanding, by the mobile device, the mobile device to provide a notification to a manufacturer of the medical device, the notification indicating the failure state.

10. The method of claim 6, wherein the instruction to prompt the patient to provide the blood sample includes a first instruction to insert a blood glucose measurement strip and a second instruction to dose the blood glucose measurement strip with the blood sample.

\* \* \* \* \*